(12) United States Patent
Nowak, Jr.

(10) Patent No.: US 7,942,917 B2
(45) Date of Patent: May 17, 2011

(54) HOLLOW HELICAL STENT SYSTEM

(75) Inventor: Thomas Nowak, Jr., North Hampton, NH (US)

(73) Assignee: Medtronic Vascular, Inc., Santa Rosa, CA (US)

(*) Notice: Subject to any disclaimer, the term of this patent is extended or adjusted under 35 U.S.C. 154(b) by 274 days.

(21) Appl. No.: 12/425,853

(22) Filed: Apr. 17, 2009

(65) Prior Publication Data

US 2010/0268314 A1    Oct. 21, 2010

(51) Int. Cl.
*A61F 2/06* (2006.01)
(52) U.S. Cl. .................................... 623/1.11
(58) Field of Classification Search ............. 623/1.11, 623/1.12, 1.15, 1.23, 1.22, 1.19; 606/191–200, 606/108; 604/523–532
See application file for complete search history.

(56) References Cited

U.S. PATENT DOCUMENTS

| | | | |
|---|---|---|---|
| 4,503,569 A | 3/1985 | Dotter | |
| 4,545,390 A | 10/1985 | Leary | |
| 4,619,274 A | 10/1986 | Morrison | |
| 4,813,925 A * | 3/1989 | Anderson et al. | 604/8 |
| 5,261,916 A * | 11/1993 | Engelson | 606/108 |
| 5,591,199 A | 1/1997 | Porter et al. | |
| 5,891,108 A | 4/1999 | Leone et al. | |
| 5,964,771 A * | 10/1999 | Beyar et al. | 606/108 |
| 6,053,900 A * | 4/2000 | Brown et al. | 604/500 |
| 6,623,519 B2 | 9/2003 | Edwin et al. | |
| 6,986,784 B1 * | 1/2006 | Weiser et al. | 623/1.1 |
| 7,122,048 B2 | 10/2006 | DiMatteo et al. | |
| 7,367,989 B2 * | 5/2008 | Eidenschink | 623/1.11 |
| 7,691,125 B2 * | 4/2010 | Ducharme | 606/200 |
| 2004/0210298 A1 * | 10/2004 | Rabkin et al. | 623/1.11 |
| 2006/0190070 A1 * | 8/2006 | Dieck et al. | 623/1.12 |
| 2007/0198076 A1 * | 8/2007 | Hebert et al. | 623/1.11 |
| 2008/0071343 A1 * | 3/2008 | Mayberry et al. | 623/1.11 |
| 2008/0255654 A1 * | 10/2008 | Hebert et al. | 623/1.11 |
| 2009/0099640 A1 * | 4/2009 | Weng | 623/1.11 |

OTHER PUBLICATIONS

U.S. Appl. No. 11/941,591 to Cook et al., filed Nov. 16, 2007.

* cited by examiner

*Primary Examiner* — Gary Jackson
*Assistant Examiner* — Christopher Schubert

(57) ABSTRACT

A stent is formed from a hollow resilient tube shaped into a helical expanded configuration to form a substantially cylindrical prosthesis that is releasably attached to an actuation shaft for delivery to a treatment site. The stent is deliverable in a substantially linear configuration and deployed with internal fluid pressure, which is delivered through the actuation shaft, to return to the helical expanded configuration. Specifically, injection of a deployment fluid into the resilient tube that forms the stent causes the stent to revert or spring back from the substantially linear delivery configuration to the original helical configuration, and in some applications to dilate a vessel. A ring is attached to a distal end of the stent to couple the stent system to a guidewire for delivery through the vasculature.

19 Claims, 3 Drawing Sheets

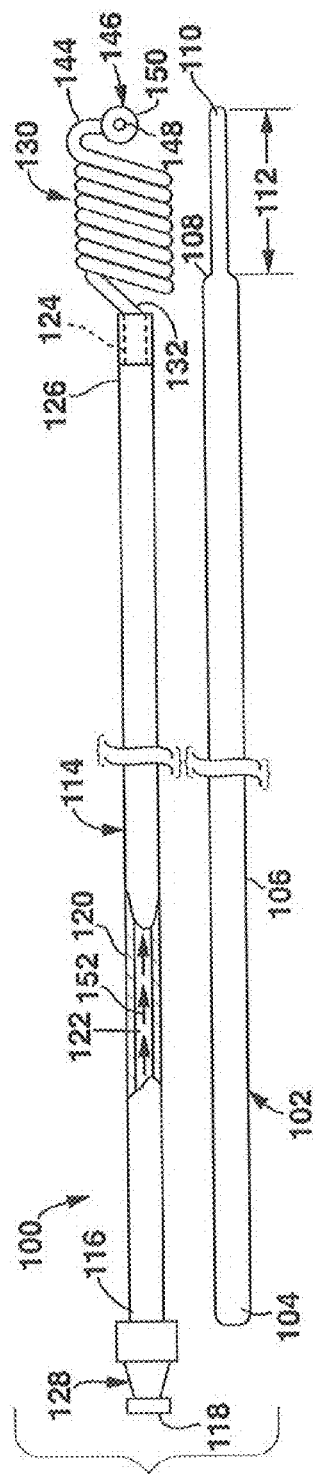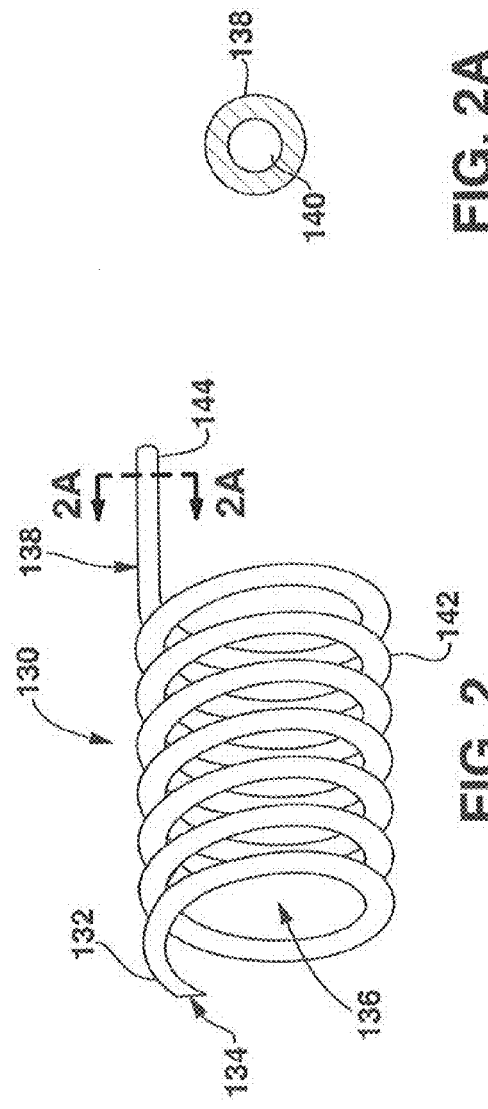
FIG. 1
FIG. 2
FIG. 2A

HOLLOW HELICAL STENT SYSTEM

FIELD OF THE INVENTION

The invention relates generally to endoluminal prostheses, and more particularly to a stent system formed from a resilient tube that is tracked through the vasculature in a substantially linear configuration and returned to an expanded helical configuration in vivo by introduction of a fluid into the stent.

BACKGROUND OF THE INVENTION

A wide range of medical treatments are known that utilize "endoluminal prostheses." As used herein, endoluminal prostheses are intended to mean medical devices that are adapted for temporary or permanent implantation within a body lumen, including both naturally occurring and artificially made lumens. Examples of lumens in which endoluminal prostheses may be implanted include, without limitation: arteries, such as those located within the coronary, mesentery, peripheral, or cerebral vasculature; veins; gastrointestinal tract; biliary tract; urethra; trachea: hepatic shunts; and fallopian tubes.

Various types of endoluminal prostheses are also known, each providing a component for modifying the mechanics of the targeted luminal wall. For example, stent prostheses are known for implantation within body lumens for providing artificial radial support to the wall tissue, which forms the various lumens within the body, and often more specifically within the blood vessels of the body.

To provide radial support to a blood vessel, such as one that has been widened by a percutaneous transluminal coronary angioplasty, commonly referred to as "angioplasty," "PTA" or "PTCA", a stent is implanted in conjunction with the procedure. Stents suitable for use in such procedures may be either self-expanding or balloon-expandable. Conventionally in a PTA procedure, the stent may be collapsed to an insertion diameter, either by crimping onto a balloon catheter or by being contained within a sheath component of a delivery catheter, and inserted into a body lumen at a site remote from the diseased vessel. The stent may then be conveyed to the desired treatment site within the affected lumen and deployed, either by self-expansion or by outward radial force provided by a delivery system such as a balloon catheter, to its desired diameter for treatment. The present invention is directed to an alternative type of stent prosthesis and an alternative method of delivering and deploying the stent prosthesis within a targeted body lumen.

BRIEF SUMMARY OF THE INVENTION

Embodiments hereof are directed to a stent system for delivering a stent within a body vessel to provide artificial radial support to a wall of the vessel. The stent system includes an actuation shaft having an elongated tubular body defining a fluid passageway and a stent releasably attached thereto. The stent is formed from a resilient tube having a fluid passageway in fluid communication with the actuation shaft lumen during delivery and deployment of the stent. The stent has a helical expanded configuration where the resilient tube forms consecutive loops with a blood flow lumen therethrough and a linear delivery configuration where the loops of the resilient tube are substantially straightened. The stent is transformable from the delivery configuration into the helical expanded configuration in vivo through introduction of a deployment fluid into the fluid passageway of the resilient tube that forms the stent. In an embodiment, the stent system includes a guidewire with an elongated body having a reduced diameter distal portion over which a ring attached to a distal end of the stent is positioned to couple the stent to the guidewire during tracking of the stent system through the vasculature.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 1 is a schematic side view of a stent system in partial section according to a prophetic embodiment of the invention.

FIG. 2 is an enlarged perspective view of the stent of FIG. 1 in its original expanded form.

FIG. 2A is a cross-sectional view of the stent of FIG. 2 taken along line 2A-2A.

DETAILED DESCRIPTION OF THE INVENTION

Figure 3:
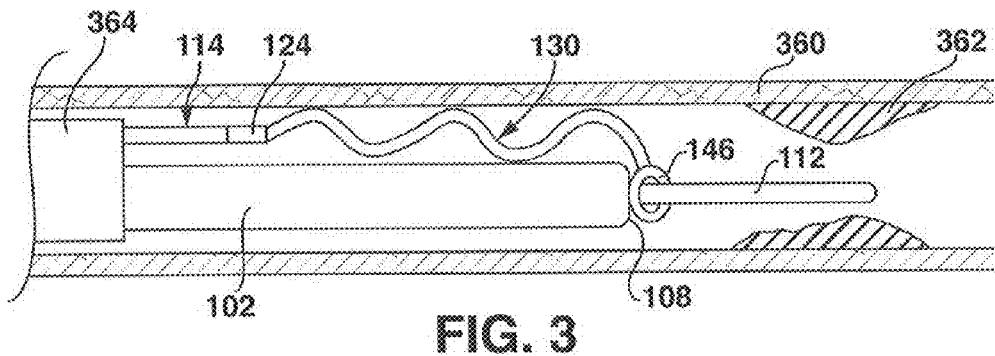
FIG. 3 is a schematic side view of the stent system of FIG. 1 being tracked to a treatment site through the vasculature.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician, "Proximal" and "proximally" are a position near or in a direction toward the clinician.

The following detailed description is merely exemplary in nature and is not intended to limit the Invention or the application and uses of the invention. Although the description of the invention is in the context of treatment of blood vessels such as the coronary, carotid and renal arteries, the invention may also be used in any other body passageways where it is deemed useful. Furthermore, there is no intention to be bound by any expressed or implied theory presented in the preceding technical field, background, brief summary or the following detailed description.

FIG. 1 is a schematic side view in partial section of a stent system 100 for delivering a stent 130 to a treatment site within the vasculature, while FIG. 2 is an enlarged perspective view of stent 130. Stent system 100 includes an elongate inflation or actuation shaft 114 with stent 130 attached to the distal end thereof, and a guidewire 102. In FIG. 1, guidewire 102 is not coupled to actuation shaft 114 and stent 130 for clarity. However, in use, actuation shaft 114 and stent 130 are releasably coupled to guidewire 102 to enable delivery of stent 130 to the treatment site.

Referring to FIGS. 2 and 2A, stent 130 is formed from a hollow resilient tube 138 shaped into a helical configuration that defines a blood flow lumen 136 through the open center of the helix. A single winding or loop 142 of stent 130 may also be described mathematically as a helical torus wherein the generally toroidal or "doughnut" shape is formed out of plane by one turn of a helix. Consecutive or adjacent loops 142 may have a stacked form, as shown in FIG. 1, or a spaced form, as shown in FIG. 2, with each loop 142 having the same outer diameter such that stent 130 has a longitudinally-extending cylindrical profile.

Resilient tube 138 of stent 130 has an open proximal end 132, which is also the proximal end of stent 130, and a closed or capped distal end 144, which is also the distal end of stent 130, with a fluid passageway 140 that extends substantially the full length of resilient tube 138. In various embodiments, resilient tube 138 has a wall thickness in the range of 0.001 to 0.015 inch with fluid passageway 140 having a diameter ranging from 0.001 to 0.125 inch. In another embodiment, fluid passageway 140 may extend for less than the full length of resilient tube 138.

Resilient tube 138 of stent 130 is formed from a biocompatible material that permits stent 130 to be substantially straightened or stretched, as shown and described with reference to FIG. 3, for delivery to the treatment site and that returns stent 130 to its original expanded helical form depicted in FIGS. 1 and 2 upon introduction of a fluid into fluid passageway 140 of resilient tube 138, as shown and described with reference to FIG. 4. Thus "resilient" as used herein to refer to tube 138 means a tube capable of resuming an original set shape or form after being stretched, elastically deformed, compressed, or the like. In an embodiment, resilient tube 138 of stent 130 is formed from an inherently elastic or spring-like material such that upon introduction of an initiation force or pressure supplied by the fluid, stent 130 has the ability to spring or revert back to the helical expanded configuration from the linear delivery configuration. In another embodiment, a material of resilient tube 138 of stent 130 may be heat set in the helical configuration in order to impart such elastic or spring-like properties thereto. Biocompatible materials that are suitable for use in embodiments hereof include polyester, polyethylene terephthalate (PET), polypropylene, nylon or other thermoplastic polyamide, polyethylene, polyether block amide copolymer (PEBA), fluoropolymers such as polytetrafluoroethylene (PTFE) or fluorinated ethylene propylene (PEP), or combinations thereof, as well as other high-modulus polymeric materials. Polymeric materials suitable for use in embodiments hereof may be biodegradable or bioresorbable such that stent 130 is absorbed in the body after being utilized to restore patency to the vessel.

In another embodiment hereof, resilient tube 138 of stent 130 may be made from a metallic material having a mechanical memory to return to the helical expanded configuration. Mechanical memory may be imparted to resilient tube 138 by thermal treatment to achieve a spring temper in stainless steel, for example, or to set a shape memory in a susceptible metal alloy, such as nitinol. In an alternate embodiment, a mechanical memory to return to the helical expanded configuration may be imparted to a polymer that forms resilient tube 138, such as any of the polymers disclosed in U.S. Pat. Appl. Pub. No. 2004/0111111 to Lin, which is incorporated by reference herein in its entirety.

Referring again to FIG. 1, actuation shaft 114 has a proximal end 116 and a distal end 126 with an elongated tubular body or shaft 120 defining a lumen 122 therebetween. Actuation shaft proximal end 116 extends proximally outside of the patient's body and is coupled to a hub 128 having an inflation port 118. Actuation shaft distal end 126 is detachably connected to stent proximal end 132, such that actuation shaft lumen 122 is in fluid communication with fluid passageway 140 of resilient tube 138. In this manner, deployment fluid 152 (depleted by arrows in FIG. 1) received through hub inflation port 118 is delivered via actuation shaft lumen 122 to deploy stent 130. In an embodiment, elongate tubular body 120 may be formed from one or more sections of flexible polymeric tubing such as tubing of polyethylene terephthalate (PET), polypropylene, nylon, polyethylene, polyether block amide (PEBA), fluoropolymers such as polytetrafluoroethylene (PTFE) or fluorinated ethylene propylene (FEP), or combinations thereof. As would be understood by one of ordinary skill in the art of catheter design, hub 128 provides a luer hub or other type of fitting that may be connected to a source of deployment fluid and may be of another construction or configuration without departing from the scope of the present invention.

In order to effectuate the transfer of pressurized deployment fluid from actuation shaft 114 to stent 130, actuation shaft 114 includes a relatively short and rigid tubular connector or blunt needle component 124 coupled to distal end 126 of elongate tubular body 120 that engages with a port 134 located at proximal end 132 of stent 130/tube 138. Connector 124 and port 134 are tightly or sealingly engaged to ensure that resilient tube 138 may be pressurized in vivo to thereby allow stent 130 to overcome its substantially linear delivery configuration and return to its original expanded helical configuration thus providing vessel wall support and/or a dilation force as discussed below. In an embodiment, port 134 includes a self-healing gasket or seal such that once connector 124 is retracted, port 134 closes. An example of a suitable self-healing or self-sealing material for use in an embodiment hereof is silicone rubber. In another embodiment, port 134 includes a polymeric ring that does not completely close upon retraction of connector 124. In such an embodiment, once stent 130 has been returned to its original helical form with the pressurized deployment fluid being used to overcome the substantially-linear delivery profile and/or to dilate a lesion, sealing of stent port 134 is not required. In another embodiment, connector 124 is sized to have an interference fit around port 134.

Guidewire 102 is a steerable guidewire having a proximal end 104 and a soft flexible tip 110 at a distal end thereof with an elongate body 106 extending therebetween. A reduced diameter distal portion 112 is demarcated by a step or taper 108 in elongate body 106 and distal tip 110. Elongate body 106 may be a solid wire or a tubular component with sufficient column strength to be pushed through a patient's vascular system without kinking and is also flexible enough to avoid damaging the blood vessel or other body lumen through which guidewire 102 is advanced. Guidewire proximal end 104 extends proximally outside of the patient's body such that it may be manipulated by a clinician and may include a handle or knob (not shown) in order to facilitate securing a longitudinal position or movement thereof. Guidewire 102 may be constructed from any suitable material, including stainless steel, Co—Ni—Cr—Mo super alloy, and NiTi alloys such as nitinol. A steerable guidewire that may be adapted for use in embodiments hereof is described in U.S. Pat. No. 4,545,390 to Leary, which is incorporated by reference herein in its entirety.

Actuation shaft 114 and stent 130 are releasably coupled to guidewire 102 by a ring 146 that is connected to distal end 144 of stent 130. Ring 146 is an annular member having an inner diameter 148 that is only slightly larger than the diameter of guidewire distal portion 112 and having an outer diameter 150 that is approximately equal to the diameter of the remainder of elongate body 106 of guidewire 102. Ring 146 slides over reduced diameter distal portion 112 of guidewire 102 to sit against step 108 during delivery such that actuation shaft 114 and stent 130 will be advanced or carried along by guidewire 102 as the guidewire is tracked through the vasculature. In an embodiment, resilient tube 138 may be shaped to form ring 146 such that ring 146 is integral or seamless with stent 130. In another embodiment, ring 146 may be a separate component that is fixedly attached to distal end 144 of stent 130 by bonding, spot welding, laser welding, using an adhesive or by any other suitable means known to one of ordinary skill in the art. In an embodiment, ring 146 may be formed from a metallic material to ensure that ring 146 will locate against or be restrained by guidewire step 108. In another embodiment, ring 146 may be formed from a radiopaque material to assist in determining placement of the stent.

A method of delivering and deploying stent 130 to a treatment site according to an embodiment hereof is described with reference to FIGS. 3-6, where the treatment site is shown to include target tissue, i.e., a lesion 362 that includes plaque obstructing blood flow through the vessel. As explained further below, pressurization of stent 130 acts to dilate lesion 362 before stent 130 is released/deployed from actuation shaft 114. In another embodiment, stent 130 may be deployed within the vessel after another revascularization procedure, such as balloon angioplasty, has been performed.

With reference to FIG. 1 above, prior to insertion into the vasculature, connector 124 at actuation shaft distal end 126 is joined to port 134 at stent proximal end 132, and actuation shaft 114 and stent 130 so joined are coupled to guidewire 102 by positioning ring 146 over guidewire distal portion 112 until ring 146 abuts step 108. FIG. 3 illustrates stent, system 100 being threaded through the vascular system of the patient until stent 130 is located at the treatment site proximate lesion 362. Access to the vasculature may be achieved, for example, through a branch of the femoral artery. In an embodiment, stent system 100 may be delivered through a guide or sheath catheter 364 in order to facilitate delivery through the vasculature. For delivery, the helical configuration of stent 130 is elastically deformed into a substantially linear delivery configuration by a clinician prior to or as stent 130 is being inserted into the vasculature, where introduction of stent 130 into guide catheter 364 may aid in the deformation process. Stent 130 is maintained in its substantially linear profile as it is tracked through the vasculature by having its distal end 144 restrained by ring 146, which is disposed against guidewire step 108, and its proximal end 132 attached to actuation shaft 114.

Figure 4:
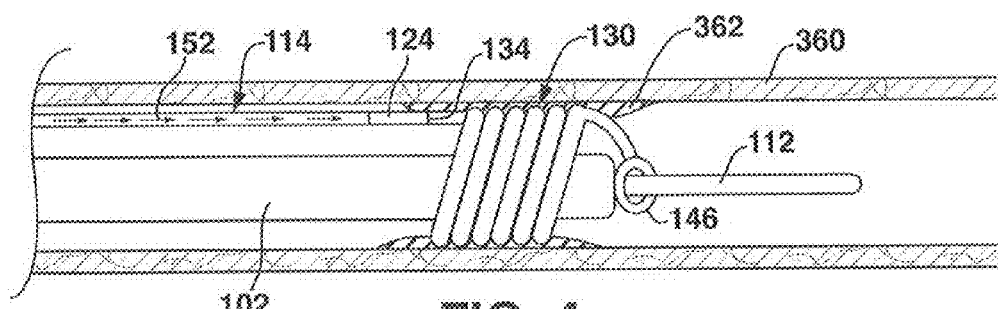
FIG. 4 is a schematic side view of the stent system of FIG. 1 being deployed at a treatment site within the vasculature.

Once stent 130 is positioned at the treatment site as desired, pressurized deployment fluid 152 is introduced as shown in FIG. 4. In embodiments hereof, deployment fluid 152 may be compressed carbon dioxide gas or an incompressible liquid such as sterile saline. Deployment fluid 152 travels through actuation shaft lumen 122 and into fluid passageway 140 of resilient tube 138. An injection of deployment fluid 152 at between 3-40 ATM of pressure into resilient tube 138 provides an initiation force or pressure that causes stent 130 to spring or cod from its substantially linear delivery configuration back into its original expanded form, viz., the helical configuration. As stent 130 reverts back to the helical configuration, resilient tube 138 coils or winds around guidewire 102 in a helical or corkscrew fashion, which may be accompanied by ring 146 freely rotating around guidewire distal portion 112. The introduction of pressurized deployment fluid within resilient tube 138 will result in a greater initial radial force being exerted by stent 130 against the target vessel wall than otherwise would be attainable with a conventional self-expanding stent, which permits stent 130 to be used for dilating lesion 362. Once deployed, stent 130 is in apposition with the vascular wall of the target vessel to maintain the opening.

Figure 5:
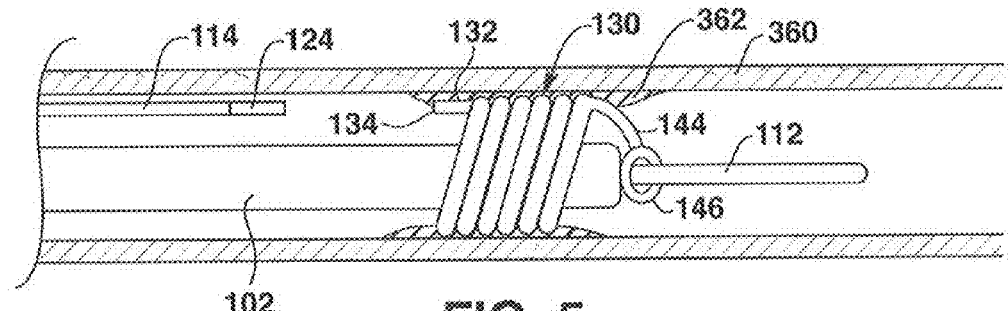
FIG. 5 is a schematic side view of the stent system of FIG. 1 deployed at a treatment site within the vasculature, with a catheter of the stent system being retracted.
Figure 6:
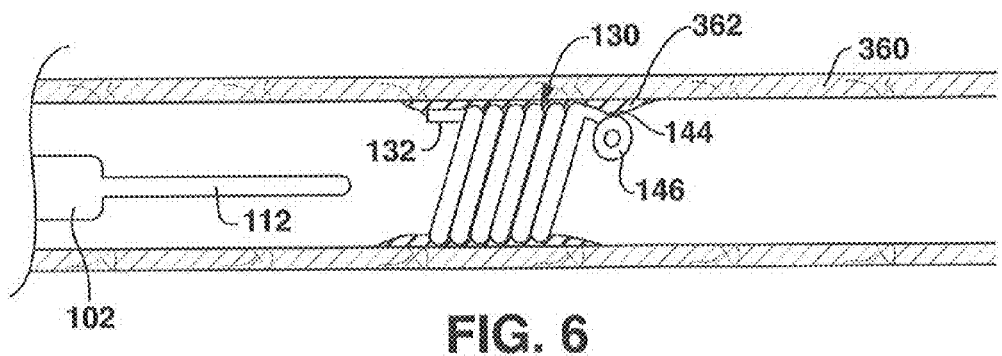
FIG. 6 is a schematic side view of the stent system of FIG. 1 deployed at a treatment site within the vasculature, with a guidewire of the stent system being retracted.

After deployment as shown in FIGS. 5 and 6, connector 124 of actuation shaft 114 may be detached from or pulled free of radially expanded stent 130 when the clinician proximally retracts actuation shaft 114 for withdrawal from the body. In an embodiment where deployment fluid 152 is compressed carbon dioxide gas or other fluid that may be desirably contained within resilient tube 138, port 134 includes a self-healing seal such that once connector 124 of actuation shaft 114 is retracted, port 134 closes to prevent leakage of the pressurized deployment fluid there from. In such embodiments, the pressurized deployment fluid provides a greater stenting force to stent 130, i.e., stent 130 has a greater resistance to compression by dilated vessel 360, which may tend to try to reclose after an interventional procedure. In another embodiment, such as where deployment fluid 156 is saline or other biocompatible fluid, port 134 may not close completely after actuation shaft 114 is retracted such that some seepage of deployment fluid 156 may occur hut would not be harmful to the patient.

In another embodiment, deployment fluid 152 may include a fixturing agent such as bone-fixturing cement. The fixturing agent changes or cures from a fluid state to a solid state after delivery into fluid passageway 140 of resilient tube 138. Once in the solid state, the fixturing agent improves the rigidity of deployed stent 130 to help maintain the opening of the blood vessel. Further, once in the solid state, the fixturing agent will not seep out of engagement port 134, if port 134 does not include a self-healing component.

As a final step in the delivery process shown in FIG. 6, guidewire 102 is proximally withdrawn from the vessel such that distal portion 112 slides through ring 146 attached to stent 130. Accordingly in this embodiment, ring 146 remains attached to stent 130 in vivo.

Figure 7:
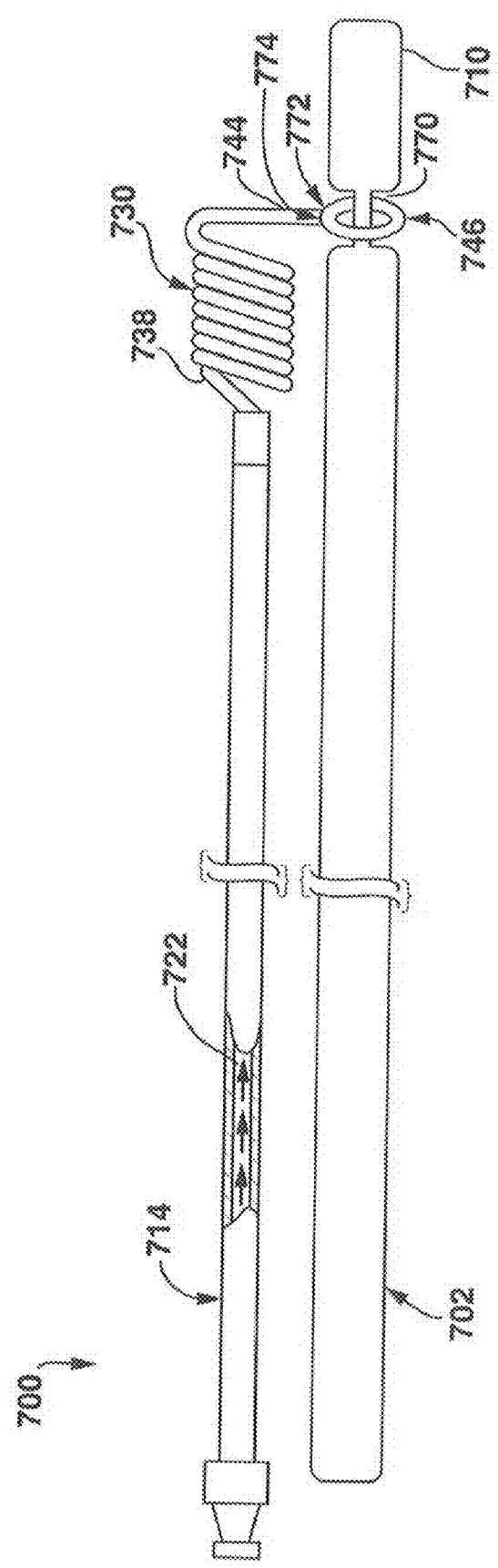
FIG. 7 is a schematic side view of a stent system according to another prophetic embodiment of the invention.

Another embodiment of a stent system 700 is shown in FIG. 7. Rather than remaining attached to deployed stent 130 as described above, a ring 746 may break away or detach from stent 730 and be removed via retraction of guidewire 702. As in the above-described embodiments, stent system 700 includes guidewire 702, inflation or actuation shaft 714 defining a lumen or fluid passageway 722, stent 730, and ring 746. As above, stent 730 is formed from a hollow resilient tube 738 defining a fluid passageway (not shown), with resilient tube 738 shaped into a helical configuration to form a substantially cylindrical prosthesis. The fluid passageway of tube 738 is in fluid communication with lumen 722 of actuation shaft 714 so that stent 730 is expanded in vivo by delivering a deployment fluid as previously discussed in detail above.

Ring 746 is attached to a distal end 744 of stent 730 at a connection 772. In this embodiment, stent 730 and actuation shaft 714 are coupled to guidewire 702 for delivery by having ring 746 located or seated within an annular groove or indentation 770 located proximal to distal end 710 of guidewire 702. "Annular groove or indentation" as used herein is intended to mean that the groove or indentation extends around the circumference of the guidewire. Similar to the above embodiments, with ring 746 seated within groove 770, stent 730 and actuation shaft 714 will be advanced or carried along as guidewire 702 is tracked through the vasculature. However after deployment of stent 730 and upon application of a force sufficient to break connection 772, ring 746 detaches from the stent and remains seated within groove 770 to be safely removed upon retraction of guidewire 702. The force sufficient to break connection 772 may be deployment, of stent 730 into radial apposition with the vessel wall, or may be retraction of guidewire 702 after deployment.

In an embodiment, resilient tube 738 is shaped to form ring 746 so that ring 746 is integral or seamless with stent 730 and includes an area of weakness 774 located at the interface of ring 746 and stent 730 to form breakable connection 772. Area of weakness 774 may include a reduced wall thickness, one or more perforations, one or more notches, or other weakened sections. In another embodiment (not shown), ring 746 may he a separate component from stent 730 and an over sleeve may be used to minimally attach the ring and the stent together for delivery. The over sleeve may have an area of weakness, as noted above, or a reduced wall thickness at the interface of ring 746 and stent 730 so that it will break or split apart upon deployment of stent 730 or retraction of guidewire 702.

In another embodiment, stents 130, 730 may be used to dilate a stenosis and then be removed from the vessel with actuation shafts 114, 714 and guidewires 102, 702. When such a method is practiced with stent system 700 shown in FIG. 7, ring 746 will remain attached to stent 730 to aid in removal of stent 730 and actuation shaft 714 with the retraction of guidewire 702. Due to the extremely low profile of stent systems 100 and 700, such dilations may be performed in tightly stenosed lesions as well as in very small diameter vessels that may not normally be dilated/accessed by balloon catheters with larger profiles.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A stent system comprising:
   an actuation shaft having an elongated tubular body defining a lumen;
   a stent releasably attached to the actuation shaft and formed from a resilient tube having a fluid passageway in fluid communication with the actuation shaft lumen, the stent having a helical expanded configuration where the resilient tube forms consecutive loops which have a blood flow lumen therethrough and a linear delivery configuration where the loops of the resilient tube are substantially straightened,
   wherein the stent is transformable from the delivery configuration to the helical expanded configuration through introduction of a deployment fluid into the fluid passageway of the resilient tube via the actuation shaft lumen;
   a guidewire with an elongated body having a reduced diameter distal portion; and
   a ring attached to a distal end of the stent, wherein the ring is slidable over the guidewire distal portion to abut a step in the guidewire.

2. The stent system of claim 1, wherein the ring is an annular member having an inner diameter only slightly larger than the guidewire reduced diameter distal portion and having an outer diameter substantially the same as the diameter of a remainder of the guidewire elongated body.

3. The stent system of claim 2, wherein the ring is fixedly attached to the distal end of the stent.

4. The stent system of claim 2, wherein the ring is an integrally formed portion of the resilient tube.

5. The stent system of claim 1, further comprising:
   a guidewire with an elongated body having an annular groove located proximal to a distal end of the guidewire with a reduced diameter; and
   a ring attached to a distal end of the stent, wherein the ring is seated within the annular groove of the guidewire.

6. The stent system of claim 5, wherein a breakable connection is formed between the ring and the stent by an area of weakness.

7. The stent system of claim 1, wherein a port is located at a proximal end of the resilient tube that forms the stent for receiving a connector attached to a distal end of the actuation shaft.

8. The stent system of claim 7, wherein the port includes a self-healing seal material.

9. The stent system of claim 7, wherein the connector is a rigid tubular component sized to have an interference fit with the port.

10. A method of using a stent system within a vessel comprising the steps of:
    introducing a stent system into the vasculature, the stent system including an elongate tubular actuation shaft defining a lumen with a stent releasably attached at a distal end of the actuation shaft and formed from a resilient tube having a fluid passageway in fluid communication with the actuation shaft lumen, the stent having a helical expanded configuration where the resilient tube forms consecutive loops which have a blood flow lumen therethrough and a linear delivery configuration where the loops of the resilient tube are substantially straightened, the stent system further including a guidewire with an elongated body having a reduced diameter distal portion and a ring attached to a distal end of the stent, wherein the ring is slidable over the guidewire distal portion to abut a step in the guidewire;
    tracking the stent system through the vasculature, wherein the stent is in the substantially linear delivery configuration;
    positioning the stent at a treatment site within the vessel;
    and introducing a pressurized deployment fluid through the actuation shaft lumen into the fluid passageway of the resilient tube that forms the stent to thereby transform the stent from the substantially linear delivery configuration into the helical expanded configuration.

11. The method of claim 10, further comprising the step of:
    detaching the actuation shaft from the stent and retracting the actuation shaft from the vessel leaving the expanded stent at the treatment site.

12. The method of claim 11, wherein a self-healing seal is located at a proximal end of the resilient tube that forms the stent which closes upon detachment of the actuation shaft such that the stent contains the pressurized deployment fluid.

13. The method of claim 10, wherein the pressurized fluid is saline.

14. The method of claim 10, wherein the pressurized fluid includes a fixturing agent that cures from a fluid state to a solid state in the fluid passageway of the resilient tube that forms the stent after the stent is returned to the helical expanded configuration.

15. The method of claim 10, wherein the catheter shaft and stent are coupled to the guidewire during the step of tracking the stent system through the vasculature.

16. The method of claim 15, wherein the reduced diameter distal portion is an annular groove in the guidewire located proximate a distal end of the guidewire.

17. The method of claim 16 further comprising the step of:
detaching the ring from the stent; and
retracting the guidewire from the vasculature with the detached ring seated within the annular groove of the guidewire.

18. The method of claim 10, wherein the step of positioning the stent at a treatment site includes positioning the stent within a stenosis in the vessel and the method further includes using the pressurized fluid to dilate the stenosis as the stent is transformed into the helical expanded configuration.

19. The method of claim 18, further comprising the step of:
retracting the stent system from the treatment site for removal from the vasculature.

* * * * *